United States Patent [19]

Gristina et al.

[11] Patent Number: 5,591,441

[45] Date of Patent: *Jan. 7, 1997

[54] COMPOSITION FOR NONSPECIFIC CELLULAR IMMUNE STIMULATION

[75] Inventors: Anthony G. Gristina, Reston, Va.; Quentin N. Myrvik, Caswell Beach, N.C.

[73] Assignee: Medical Sciences Research Institute, Herndon, Va.

[*] Notice: The portion of the term of this patent subsequent to Mar. 8, 2011, has been disclaimed.

[21] Appl. No.: 197,340

[22] Filed: Feb. 16, 1994

Related U.S. Application Data

[63] Continuation of Ser. No. 885,301, May 18, 1992, Pat. No. 5,292,513.

[51] Int. Cl.$^6$ .............................. A61K 9/14; A61F 2/02; A61L 9/04

[52] U.S. Cl. .................. 424/401; 424/45; 424/85.1; 424/85.2; 424/426; 424/434; 424/435; 424/489; 424/499; 424/501; 514/885

[58] Field of Search .......................... 424/45, 85.1, 85.2, 424/423, 434, 435, 489, 426, 499, 501; 514/885; 435/7.24; 436/822; 428/402

[56] References Cited

U.S. PATENT DOCUMENTS

| | | | |
|---|---|---|---|
| 4,707,471 | 11/1987 | Larm et al. | 514/54 |
| 4,783,484 | 11/1988 | Violanto et al. | 514/535 |
| 4,795,745 | 1/1989 | Larm et al. | 514/54 |
| 4,826,689 | 5/1989 | Violanto et al. | 424/489 |
| 4,900,722 | 2/1990 | Williams et al. | 514/54 |
| 4,971,801 | 11/1990 | Urban | 424/450 |
| 5,004,604 | 4/1991 | Terness et al. | 530/389.3 |
| 5,045,320 | 9/1991 | Mescher | 424/450 |
| 5,078,996 | 1/1992 | Conlon et al. | 424/85.1 |
| 5,091,511 | 2/1992 | Sone et al. | 530/351 |

OTHER PUBLICATIONS

Kingo Chida et al., Chemiluminescent Response of Alveolar Macrophages, Infect. Immun., vol. 55, No. 6, Jun. 1987.
Hiroshi Hayakawa et al., Oxidative Responses of Rabbit Alleolar Macrophages, J. of Leukocyte Biology, 45 (1989).
Q. N. Myrvik et al., S.epidermidis Slime and Alveolar Macrophages, Journal of Investigative Surgery, vol. 2.
Keiko Umehara et al., L-Fucose Blocks MIF/MAF Priming, Cellular Immunology 119, (1989).
G. Giridhar et al., HSV-2 Infection and CL Response in Rabbit AM, Journal of Leukocyte Biology 49:442-448 (1991).

(List continued on next page.)

Primary Examiner—Carlos A. Azpuru
Attorney, Agent, or Firm—Whitham, Curtis, Whitham & McGinn

[57] ABSTRACT

A non-specific host immune cell augmentation composition for enhanced microorganism killing utilizes any phagocytosable, biocompatible particle to prime macrophages for enhanced oxidative response and bacterial killing. Patients can have the benefits of primed macrophages in one to four days, and experiments have demonstrated over a 100-fold increase in oxidative potential within this time period. The oxidative response and killing potential is non-immunospecific, meaning not one organism, not a vaccine, and broadly applicable simultaneously to bacteria and viruses as well as tumor cells. The effects have been demonstrated to have a seven day duration to have a seven day duration indicating non-tissue toxic residual effects and potential for repeated use at monthly intervals.

11 Claims, 1 Drawing Sheet

OTHER PUBLICATIONS

A. Bautista et al., In vivo latex phagocytosis primes . . ., Journal of Leukocyte Biology, vol. 51, Jan. 1992.

K. E. Driscoll et al., Release of Interleukin–1 and Tumor Necrosis . . ., NATO ASI Series vol. H30.

K. Donaldson et al., Release of Superoxide Anion and Hydrogen Peroxide . . ., NATO ASI Series, vol. G3.

Rolf Seljelid, Immunomodulator–Medicine for the 90–ies?, Immunomodulators, pp. 107–113.

Hiroshi Hayakawa et al., Pulmonary Surfactant Phospholipids Modulate . . ., Journal of Leukocyte Biology.

Bernard M. Babior et al., Oxygen–Dependent Microbial Killing by Phagocytes, New England Journal of Medicine.

Seymour J. Klebanoff, Oxgen–Dependent Cytotoxic Mechanisms of Phagocytes, Adv.in Host Defense Mechanisms.

K. Donaldson et al., Chemiluminescence of asbestos–activated macrophages, Br.J.exp.Path.(1984) 65, pp. 81–90.

COMPOSITION FOR NONSPECIFIC CELLULAR IMMUNE STIMULATION

This invention was made with government support under AR26957 and GM35939, both of which were awarded by the National Institutes of Health. The government has certain rights in the invention.

This is a continuation of application Ser. No. 07/885,301, filed May 18, 1992, now U.S. Pat. No. 5,292,513.

DESCRIPTION

1. Phagocyte-a cell that engulfs bacteria and other foreign particles by phagocytosis.
2. Macrophage-a cell derived from the reticuloendothelial system that functions in phagocytosis. Macrophages are phagocytes.
3. Activate-transforming a cell from a resting state to one where it actively performs its biological function. For example, a macrophage or phagocyte is activated when it encounters a foreign object. Upon encountering the foreign object, the macrophage releases a respiratory burst of oxidizing chemicals to kill or otherwise destroy the object.
4. Elicit-to evoke a response from a cell. For example, foreign objects might be provided to macrophages to elicit the respiratory burst activity.
5. Priming-converting a cell from one state to another, whereby its primed state is more active to a biological substance than if the cell had not been primed. In this patent, the difference between priming a macrophage, as opposed to activating a macrophage or eliciting a response, is very important.
6. Cytokine-a group of substances formed by an animal in response to infection. Cytokines are similar to hormones in their function, whereby they are produced in one cell and stimulate a response in another cell. Cytokines includes such substances as interferon, interleukin, and tumor necrosis factor.

BACKGROUND OF THE INVENTION

Field of the Invention

The invention is generally related to priming macrophages for enhanced killing potential. More particularly, the invention includes administering a priming factor to a patient so that the macrophages in the patient will be primed for enhanced killing activity a certain number of days after the priming factor was administered.

Description of the Prior Art

It is now well understood that phagocytes, such as alveolar macrophages and the like, play an important role in controlling microbial infections. Baboir, *New Eng. J. Med.*, 298:659–68 (1978), has explained that upon encountering a foreign material, such as an invading bacterial cell, phagocytes produce a respiratory burst wherein highly oxidative species, such as superoxide anion ($O_2^-$), singlet oxygen ($O_2$), and hydrogen peroxide ($H_2O_2$), are produced. The purpose of the respiratory burst is to provide a battery of oxidizing agents that can be used by the phagocyte for the destruction of invading micro-organisms and other foreign material. Many agents, both particulate and soluble, are able to activate the respiratory burst. Particulate activating agents include opsonized bacteria, zymosan (a preparation of yeast cell walls), and latex spheres. Among the soluble activating agents are phorbol myristate acetate, a complex plant product; a variety of ionophores; the complement C5a; and fluoride ion. Activation may not require phagocytosis; rather, simply contact of the foreign stimulant with the phagocyte surface may be enough to activate the phagocyte to produce the respiratory burst. The oxygen-dependent cytotoxic mechanisms of phagocytes are discussed at length in Klebanoff, *Adv. Host Def. Mech.*, (Vol. 1, eds. J. Gallin and A. Fauci, Raven Press, New York 1982 pp.111–163).

Baboir also explains that the respiratory burst activity can be detected by monitoring the chemiluminescence phenomena wherein light emission accompanies activation of the phagocyte. The light emission stems from the oxidative species produced by the phagocyte. For example, singlet oxygen is an electronically excited state of oxygen that can revert spontaneously to atmospheric oxygen, and this reversion is accompanied by a pulse of light. However, it is now generally believed that superoxide anion is responsible for the chemiluminescent response.

Many researcher groups have used chemiluminescence to study macrophage activity. For example, Donaldson et al., *Br. J. exp. Path.*, 65:81–90 (1984), used chemiluminescence measurements to show that macrophages treated with chrysotile asbestos and *Cornyebacterium parvum* elicited greater levels of reactive oxygen species than saline treated macrophages. In addition, Donaldson showed that peritoneal exudate cells harvested from $CF_1$ mice five days after injection with chrysotile asbestos or *C. parvum* had a approximately a two to three fold increase in measured chemiluminescence. Donaldson et al. suggest that the asbestos-activated macrophages are primed to produce increased amounts of reactive oxygen species which could be triggered by a number of inhalable particles (e.g., bacteria, yeast, pollen, and asbestos itself), and that an excess of these reactive oxygen species in the alveolar spaces leads to epithelial damage and ultimately to fibrosis. Other examples where chemiluminescent response measurements were used include: Chida et al., *Infect. Immun.*, 55:1476–1483 (1987), reports on a study where infant and mature rabbits were vaccinated with the heat killed Bacillus Calmette Guerin (BCG) strain of *Myobacterium bovis* and shows that the alveolar macrophages (AM) of infant rabbits were poor responders to phorbol myristate acetate (PMA)-induced chemiluminescent responses compared to AM from older rabbits which were vaccinated with BCG, thus illustrating a deficiency in the AM of neonatal and infant animals that may account for their increased susceptibility to pulmonary infections; Hayakawa et al., *J. Leuk. Biol.*, 45:231–238 (1989), reports on a study where a chemiluminescent assay was used to show that AM from BCG vaccinated rabbits (3 weeks after i.v. injection), when cultured in vitro with various serum preparations, could result in significant changes in the chemiluminescent (CL) response; Myrvik et al., *J. Invest. Surg.*, 2:381–389 (1989), reports on a study where extracellular slime from *Staphyloccocus epidermis* was found to affect the CL response on PMA-induced rabbit AM; Umehara et al., *Cell. Immun.*, 119:67–72 (1989), reports on a study where CL responses were used to show L-Fucose blocks migration inhibition factor (MIF)/macrophage activation factor (MAF) priming of rabbit AM (PMA-induced oxidative response used); Giridhar et al., *J. Leuk. Biol.*, 49:442–448 (1991), reports on a study where CL responses were used to show priming of rabbit AM by herpes simplex virus type 2 infection.

There has been much effort made in finding materials which can provide protection from infection. U.S. Pat. Nos. 4,707,471 and 4,795,745 to Larm et al. disclose that pretreatment with water soluble aminated β-1,3-D-glucans can stimulate the activity of macrophages such that animals are protected from virulent pneumococci. U.S. Pat. No. 5,045,320 to Mescher discloses that immunization with a solid support having a variety of different ligands attached can elicit and augment T cell mediated responses. U.S. Pat. No. 4,900,722 to Williams et al. discloses a class of phosphorylated glucans useful in the treatment of infections. U.S. Pat. No. 5,078,996 to Conlon et al. discloses the use of granulocyte stimulating factor to activate macrophage tumoricidal activity. U.S. Pat. No. 3,119,741 discloses an acylated bacterial lipopolysaccharide useful as a non-specific immunological agent.

There is a need for a short-term, non-specific therapeutic which provides protection against a wide variety of bacterial and viral infections. Such a therapeutic could ideally be used in anticipation of events which lead to infections such as surgery, biological warfare, natural disasters and the like. Up-regulation of the macrophage oxidative killing potential could be beneficial to such an end; however, the time duration for such priming would advantageously be limited so as to avoid cellular and matrix protein damage, fibrosis, and other injuries which would occur from the chronic production of reactive oxygen species.

SUMMARY OF THE INVENTION

It is therefore an object of this invention to provide an immunomodulation technique for non-specific cellular immune stimulation.

It is another object of this invention to provide a method for up-regulating macrophages for a short duration by using phagocytosable particulates to prime the macrophages for a short period of time.

It is yet another object of this invention to provide compositions suitable for use in priming macrophages for enhanced killing potential.

According to the invention, macrophages can be primed for a markedly enhanced oxidative response by injecting a patient with phagocytosable particles a few days before the enhanced activity is required. Experiments suggest that the primed macrophages could have greater than 100 times the activity potential than normal, non-primed macrophages. However, the priming is for a short duration and wears off to normal after a week so that the treatment process does not pose long term hazards for enhanced in vivo reactive oxygen production.

In the experiments, adult rabbits were injected intravenously (i.v.) with phagocytosable (1–5 μm) particulate preparations such as zymosan, latex particles or heat-killed BCG. The preparations primed AM rapidly in 1–4 days for greatly enhanced phorbol myristate acetate (PMA) or opsonized zymosan (Op-zym) elicited chemiluminescent (CL) responses. AM obtained from particle injected rabbits showed more than 100-fold higher levels of CL responses than AM from normal rabbits. Specifically, AM from resident rabbits normally generate about 3,000 cpm when challenged with PMA, whereas AM from rabbits injected i.v. with 20 mg of zymosan three days prior to harvesting AM, generated up to 900,000 cpm when challenged with PMA. In contrast, the particles failed to prime normal AM in vitro for enhanced CL responses. Furthermore, AM could not be primed in vivo with non-phagocytosable (~25 μm diameter) particles. The priming effect was of short duration and declined 5 to 7 days after injection of the particle preparations. It was also observed that AM from normal rabbits could be primed in vitro for enhanced CL responses by incubating AM for 3 to 18 h with the lung lavage fluids obtained from particle-primed rabbits which suggests the presence of a macrophage priming factor(s) in the lung lavage fluid.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
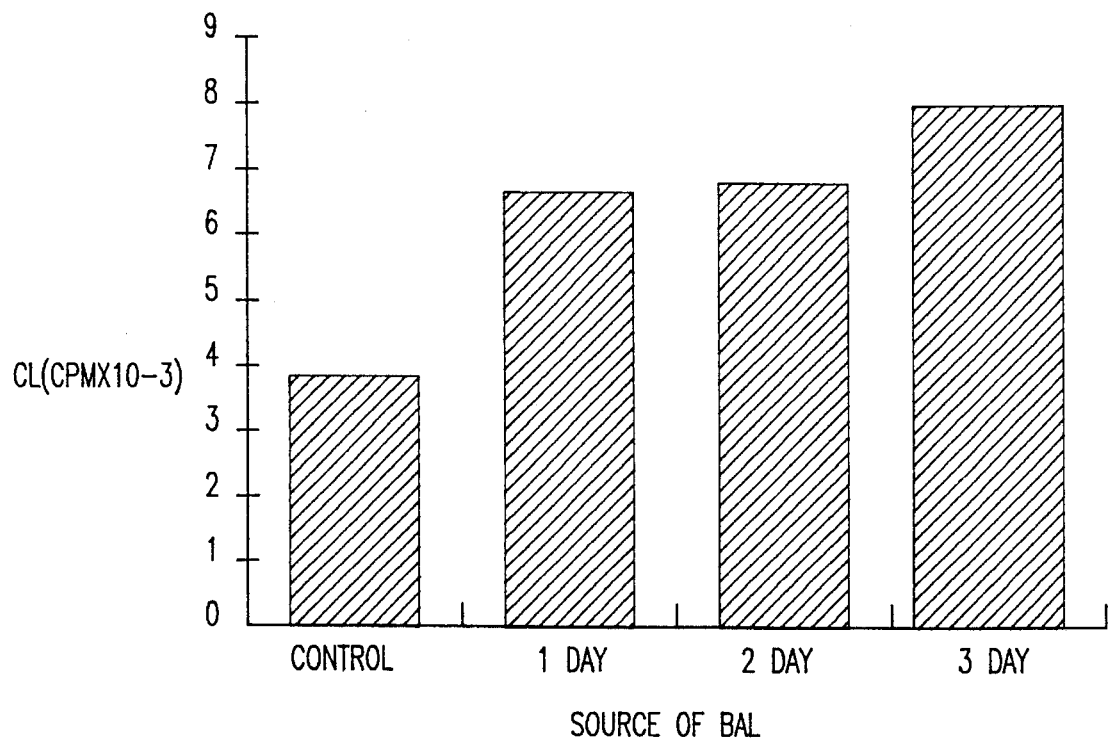
FIG. 1 is a graph showing in vitro priming of normal rabbit AM with BAL extracted from rabbits injected with zymosan 1, 2, or 3 days prior to harvesting AM for enhanced PMA-elicited CL responses.

A number of experiments have been performed which demonstrate that phagocytosable particles are effective for up-regulating macrophages for short duration.

1. Materials and Methods

Reagents

Tissue culture reagents were purchased from Curtin Matheson Scientific Company, Inc. (Columbia, Md.). Polystyrene and PMMA latex particles were purchased from Polysciences, Inc. (Warrington, Pa.). Other chemicals were purchased from Sigma Chemical Company (St. Louis, Mo.) unless otherwise specified.

Animals

New Zealand white SPF rabbits of either sex, 4–5 months old, were purchased from Hazleton Research Products, Inc. (Denver, Pa.). The animals were housed for 3–4 days in our animal facility to allow the animals to adjust to their new environment before being used.

Collection of macrophages

Rabbits were sacrificed by pentobarbital given i.v. (75–85 mg/kg) or rabbits were anesthetized with Ketamine/rompon (40 mg/kg and 5–10 mg/kg i.m.) and then exsanguinated or given air embolism while under anesthesia. AM were harvested by lung lavage technique described in Myrik et al., *J. Immunol.* 86:128–132 (1961), which is herein incorporated by reference, using 200 ml of cold saline. The harvested cells were washed 3X by centrifugation (200×g, 10 min) in RPMI 1640 medium (pH 7.2) containing penicillin (100 U/ml), streptomycn (100 μg/ml), and L-glutamine (2 mM), but without phenol red and serum. The cells were resuspended in the same medium to obtain a cell density of $3 \times 10^7$ cells/ml.

Cell viability

The viability of the AM was determined by trypan blue (0.25%) exclusion staining.

Protocol for in vivo priming of rabbit AM

To prime AM in vivo, adult rabbits were injected i.v. with 10 mg of heat-killed BCG strain of *Mycobacterium bovis* suspended in 4 ml of saline or with 20 mg of zymosan in 2 ml of saline. The AM were harvested 1 to 7 days after injection.

Chemiluminescence assay

The CL response was assayed by a previously described procedure of Girdhar et al., *J. Leuk. Biol.* 49:442–448 (1991), which is herein incorporated by reference. The assay was done in diffused light using dark-adapted 3.5 ml polypropylene scintillation vials. A typical assay mixture consisted of 3 ml Hanks' Balanced Salt Solution (HBSS) (pH 7.2) at 37° C., 0.1 ml cell suspension (3×10$^6$ cells), and 30 µl, 0.5 µg/ml), latex (7.5 µl, 250 µg/ml), Polybead Polystyrene Microspheres, 2.5% solid latex of 1.03 µm diameter, or opsonized zymosan (Op-zym), (30 µl; 100 µg/ml) were added to elicit the CL response. The counts per minute (cpm) were recorded by scintillation spectrometry using a Beckman LS 100 C scintillation counter.

Collection of bronchoalveolar lavage fluids (BAL)

BAL were collected from control as well as particle-primed rabbits. Lungs removed from rabbits were lavaged using 100 ml of cold saline, and the fluids were centrifuged at 300×g for 10 min to remove the cells and cell debris. The supernatant fluids were centrifuged at 60,000×g for 2 h at 4° C., and the supernatant fluids were filtered (0.45 µm pore size) and used as crude BAL containing the putative macrophage priming factor (MPF).

In vitro priming of normal rabbit AM with BAL

Freshly-harvested AM from normal rabbits were incubated with various concentrations (10 to 100%) of BAL from primed animals for 3 to 18 h in RPMI 1640 medium at a cell density of 1×10$_6$/ml in Teflon flasks. After incubation, the cells were washed 2× with RPMI 1640 medium and assayed for a CL response with PMA or OP-zym as tile eliciting agents. AM incubated with or without BAL from normal animals served as controls.

2. Experiments

In vivo priming of AM in adult rabbits following zymosan administration for enhanced oxidative responses Adult rabbits were injected i.v. with 20 mg of zymosan particles in 2 ml of saline. On the days following injection, the animals were sacrificed, AM was harvested, and either PMA or Op-zym was used to elicit chemiluminescence from the harvested AM. Table 1 presents the measured cpm*10$^{-4}$±SEM for the two eliciting agents on the test days.

TABLE 1

| Days After Priming | Oxidative Responses (CPM * 10$^{-4}$) Eliciting Agents | |
|---|---|---|
| | PMA | Op-zym |
| 0 (control; no injection) | 0.3 ± 0.5 | 7 ± 2.5 |
| 1 | 7.0 ± 1.1 | 17 ± 3.8 |
| 2 | 25 ± 5.2 | 45 ± 8.3 |
| 3 | 92 ± 10.1 | >100 |
| 4 | 7 ± 2.5 | 12 ± 2.4 |
| 5 | 5 ± 0.3 | 21 ± 2.2 |
| 7 | 4 ± 0.4 | 25 ± 8.5 |

Table 1 shows a very dramatic short-term priming effect caused by the injected particles. While the CPM values increased immediately after injection, unusually high levels of PMA- or Op-elicited oxidative responses was observed when particles were administered three days prior to harvest. AM harvested three days after zymosan injection generated a PMA-elicited CPM of more than 900,000 and Op-zym-elicited CPM were greater than 1,000,000. In addition, an increase in the resting values from less than 500 CPM for normal AM to about 2,000 CPM for primed AM was also observed (resting values being the CPM when no eliciting agent was provided). The decline in the oxidative response observed from days 4 to 7 demonstrates that the observed particle induced priming of the macrophages was for only a short duration.

Alternate modes of administration, such as intratracheal microdroplet instillation (e.g., aerosols and the like), yielded similar results. Adult rabbits were injected intratracheally (i.t.) with 20 mg of zymosan in 2 ml of saline four days prior to harvesting their AM. Control rabbits received 2 ml of saline. The harvested AM were assayed for CL responses with PMA or Op-zym as eliciting agents. Table 2 presents data showing enhanced oxidative responses for AM obtained from rabbits injected i.t. with zymosan (data represent three separate experiments).

TABLE 2

| Particle injected | Oxidative responses (CPM * 10$^{-4}$) Eliciting Agents | |
|---|---|---|
| | PMA | Op-zym |
| Saline (control) | 0.2 | 5.1 |
| Zymosan (20 mg) | 14.6 | >100 |

Table 2 shows that AM from rabbits injected i.t. with 20 mg of zymosan 4 days prior to harvesting AM generated Op-zym elicited CL responses of more than 1,000,000 CPM.

Cell Analysis of Lavagates from Zymosan-Injected Animals and evidence that AM are Involved in the Priming Response.

Adult rabbits were injected i.v. with 20 mg of zymosan in 2 ml of saline. Groups of rabbits were sacrificed and the cells (AM) were harvested by lavage 1, 2, 3, or 4 days after zymosan injection. The viability of the cells was determined by the trypan blue exclusion test and differential cell counts were determined by evaluating cytocentrifuge slide preparations stained with Wright-Giemsa solution. Table 3 presents the differential numbers of AM, lymphocytes (Lym) and polymorphonuclear leukocytes (PMN) from normal and zymosan injected adult rabbits (results are ±SEM (n=4)).

TABLE 3

| Days After iv injection | Differentiation of Cell Counts | | |
|---|---|---|---|
| | AM | Lym | PMN |
| Control | 95.5 ± 22.0 | 5.0 ± 1.1 | 1.1 ± 0.2 |
| 1 | 72.2 ± 15.5 | 1.9 ± 0.7 | 24.7 ± 13.8 |
| 2 | 78.5 ± 9.3 | 5.5 ± 2.6 | 16.2 ± 8.2 |
| 3 | 84.8 ± 0.8 | 9.0 ± 1.0 | 6.3 ± 2.2 |
| 4 | 95.4 ± 5.3 | 2.8 ± 3.1 | 1.9 ± 2.2 |

Table 3 shows that total neutrophils comprised about 25% of the total recovered on day 1, 16% on day 2, 6% on day 3 and 2% on day 4. In view of the fact that AM from zymosan-injected rabbits exhibited about a 20 to 200-fold increase in Op-zym or PMA elicited CL responses compared to AM from control rabbits (Table 1), and that the in vivo priming effect was highest on day 3 when the AM population was 85% and the PMN population was only about 6% of the cells harvested (Tables 1 and 3), the data establish AM was the predominant cell population involved in the generation of the oxidative burst.

Comparative in vivo priming of AM from adult rabbits following i.v. injection of zymosan, HK-BCG or latex particles To study the comparative effects of other particles on priming macrophages, adult rabbits were injected i.v. with 20 mg latex in 2 ml saline, 20 mg zymosan in 2 ml of saline, or 10 mg heat killed (HK)-BCG in 4ml of saline two days prior to harvesting AM. Oxidative responses were then elicited by PMA (0.5 µg/ml), latex (100 µg/ml) or opsonized zymosan (100 µg/ml). Table 4 presents data showing the in vivo priming of adult rabbit AM by zymosan, HK-BCG, and latex for enhanced oxidative responses elicited by PMA, latex, and op-zym.

TABLE 4

| Particles injected | Conc. (mg) | Oxidative Responses (CPM * 10⁻⁴) Eliciting Agents | | |
|---|---|---|---|---|
| | | PMA | Latex | Op-zym |
| Control | 0 | 0.25 ± 0.03 | 0.5 ± 0.2 | 7.5 ± 1.5 |
| Zymosan | 20 | 6.2 ± 0.3 | 11.5 ± 2.2 | 46.0 ± 3.6 |
| HK-BCG | 10 | 8.3 ± 0.4 | | >100 |
| Latex | 20 | 3.3 | | 14.9 |

Table 4 shows that HK-BCG and latex particles were also highly effective in priming normal rabbit AM in vivo for markedly enhanced CL responses. Preliminary results with other particles have been similar. The results indicate that the in vivo priming of normal rabbit AM is non-specific with respect to the types of particle preparations injected into the rabbits as well as with respect to the eliciting agents. It is preferable that the particles that are administered be biodegradable within a few days after their priming function is fulfilled. Specifically, particles should remain substantially intact for 1–4 days to achieve the priming function presented in the above tables; however, after the fourth day, when the priming function has been found to diminish (Table 1), the particles would preferably be broken down by bodily functions so that the particles themselves would not present a medical challenge to the patient.

Failure of Non-phagocytosable (~25 μm) latex particles to prime AM in vivo

In the above experiments, the particles employed were phagocytosable (e.g., 1–5 μm in diameter). To determine whether the size of the particle plays an important role in priming the macrophages, adult rabbits were injected i.v. with 20 mg of non-phagocytosable latex particles on the order of 25m in diameter. The latex beads were suspended in 2 ml of saline. AM were harvested two days after injection and assayed for PMA or Op-zym elicited CL responses. Table 5 shows that i.v. injection of adult rabbits in vivo with 20 mg of non-phagocytosable latex particles approximately 25 μm in diameter did not result in priming AM.

TABLE 5

| Source of AM | Oxidative Responses (CPM * 10⁻⁴) Eliciting Agents | |
|---|---|---|
| | PMA | Op-zym |
| Control Rabbit | 0.4 ± 0.1 | 7.0 ± 1.1 |
| Latex-injected Rabbit | 0.8 ± 0.09 | 0.6 ± 0.05 |

Table 5 clearly shows that priming which results from prior treatment with non-phagocytosable particles was insignificant. Contrasting Table 5 with the results above, clearly the size of the particle plays an important role in priming macrophages for enhanced killing potential.

Failure of zymosan to prime normal AM in vitro

To determine whether zymosan particles can prime normal resident AM in vitro, freshly harvested AM from normal rabbits were incubated with 5 mg zymosan/ml of AM suspension in RPMI 1640 medium for 18 hours at 37° C. in 5% $CO_2$. AM incubated without zymosan served as controls. After incubation, the cells were washed and assayed for CL responses using PMA as the eliciting agent. Table 6 shows that zymosan particles did not prime normal AM in vitro for enhanced oxidative responses as they did when injected i.v. into rabbits.

TABLE 6

| Treatments of AM | Chemiluminescence (CPM * 10⁻⁴) | |
|---|---|---|
| | Resting | Peak |
| AM indicated alone | 0.1 ± 0.02 | 2.5 ± 1.1 |
| AM incubated with zymosan | 0.06 ± 0.01 | 0.4 ± 0.06 |

Table 6 shows that incubating AM for 18 hours with zymosan particles actually resulted in a reduced level of the oxidative responses. Incubating normal AM for 18 h resulted in an enhanced PMA-elicited CL responses (25,000 CPM) compared to the level of CL responses generated by freshly harvested AM (3,000 to 5,000 CPM). This phenomenon was referred to as "spontaneous priming" by Hayakawa et al., *J. Leuk. Biol.*, 45:231–238 (1989), which is noted above.

In vitro priming of normal AM with bronchoalveolar lavage fluids (BAL) produced from zymosan injected rabbit.

FIG. 1 shows that when freshly harvested AM from normal rabbits were incubated for three hours with BAL procured from rabbits injected with zymosan particles three days prior to harvesting cells, it primed normal AM for more than as 2-fold increase in PMA-elicited CL responses compared to untreated AM. In FIG. 1, rabbits were injected i.v. with 20 mg of zymosan in 2 ml of saline three days prior to extracting BAL. AM harvested from control rabbits were incubated for three hours at 37° C. with BAL preparations (50%) and were subsequently assayed for oxidative responses with PMA as the eliciting agent. It is noted that the level of oxidative burst by AM primed in vitro with BAL was much lower compared to in vivo priming with particle injection (see Table 1 above).

Figure 2:
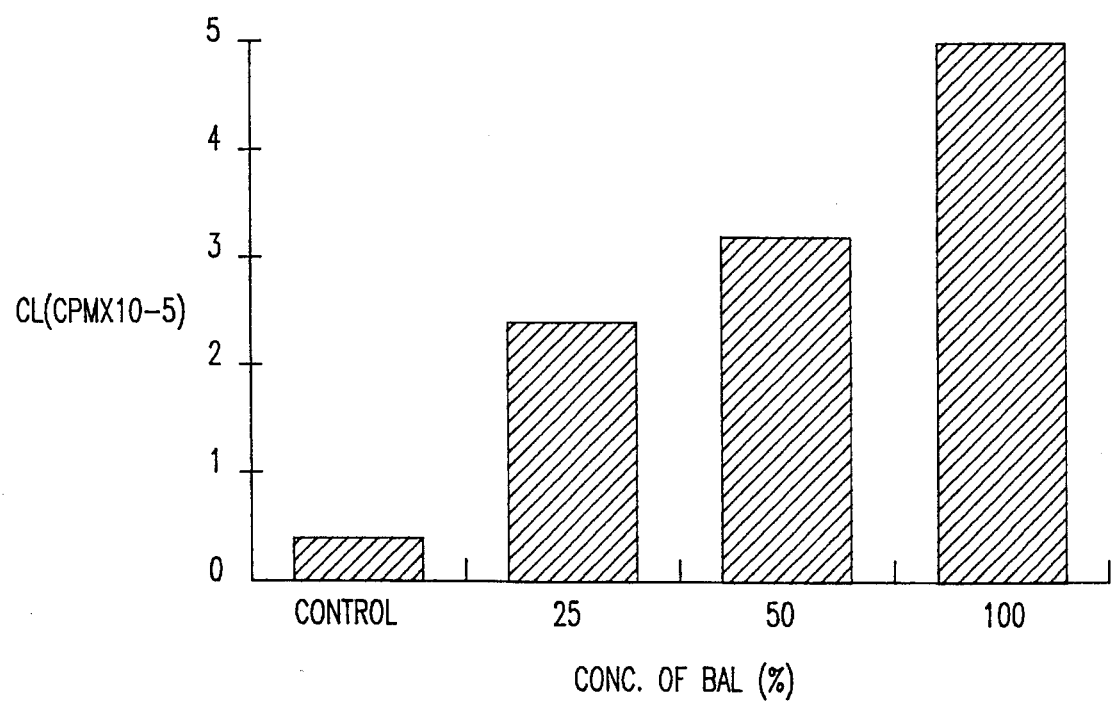
FIG. 2 is a graph showing in vitro priming of normal rabbit AM with various concentrations of BAL extracted from zymosan injected rabbits for enhanced latex elicited CL responses.

FIG. 2 shows that when AM from normal rabbits were incubated for 18 h with various concentrations of BAL fluids procured from zymosan injected rabbits, BAL fluids primed normal AM for as high as a 15-fold increase in latex elicited CL responses compared to that observed with untreated AM. In FIG. 2, BAL was extracted from rabbits two days after i.v. injection with 20 mg of zymosan. AM harvested from control rabbits were incubated with various concentrations of BAL for 18 hours at 37° C. and subsequently assayed for CL responses with latex as the eliciting agent. FIG. 2 shows that incubation of normal AM with lavage fluids procured from normal rabbits did not prime normal AM.

FIGS. 1 and 2 indicate that BAL fluids of zymosan-injected rabbits contain a macrophage priming factor (e.g., a cytokine) capable of priming macrophages that have not been exposed to particles. Only the BAL fluids of zymosan-injected rabbits contained a macrophage priming factor(s) that can prime normal AM in vitro. It is anticipated that the macrophage priming factor can be isolated and administered to patients instead of the phagocytosable particles to achieve the short duration priming effect shown in the data above. Hence, patients would be provided (e.g., by injection (intravenous, intratracheal, intraperitoneal, intramuscular, subcutaneous etc.), aerosol, or other means such as suppository, oral or nasal delivery, etc.) with a preparation containing the macrophage priming factor so that the macrophages in that patient could be primed for enhanced killing potential a certain number of days after such administration. It was observed that the macrophage priming factor present in BAL is relatively unstable and that about 50% of its activity is lost on storage at −60° C. over a 15-day period.

3. Applications

The important points discovered in the above experiments were: (1) the injection of adult rabbits with particulate preparations (zymosan, latex, or HK-BCG) of phagocytosable size prime AM in vivo in 1 to 4 days to give a very large oxidative burst when elicited in vitro with PMA, Op-zym or latex; (2) AM cannot be primed in vitro with the particulate preparations used; (3) AM are not primed in vivo by injecting large non-phagocytosable particle preparations; and (4) normal AM are primed in vitro with BAL procured from zymosan injected rabbits.

It is of particular interest that the magnitude of the elicited oxidative burst observed in the experiments of AM primed by i.v. injection of particulate preparations was equal to the maximal priming achieved three weeks after immunization with heat-killed BCG in oil (See, Chida et al., *Infect. Immun.*, 55:1476–1483 (1987), Giridhar et al., *J. Leuk. Biol.*, 49:442–448 (1991), and Hayakawa et al., *J. Leuk. Biol.*, 45:231–238 (1989)). This level of response is indeed impressive because it represents more than a 100-fold increase in the capacity of AM to generate oxygen radicals as compared to resident AM from normal animals when elicited in vitro. This response is markedly different from classical T cell-mediated priming of macrophages in that the post-injection interval is only two to three days before maximal priming is observed.

The fact that AM cannot be primed in vitro with the particulate preparations used is of particular interest. This suggests that a second cell type may be involved in the priming of AM. A requirement of a particle of phagocytosable size is also notable. We were unable to induce any detectable priming of AM with non-phagocytosable latex particles. The requirement that particles must be of phagocytosable size suggests that phagocytosis of the injected particulates triggered the production of some macrophage-derived cytokine that activated a secondary cell type, such as a lymphoid, which is ultimately responsible for production of a priming factor(s). In this regard, either interleukin-1 or tumor necrosis factor could be candidates for activating the cell that ultimately synthesizes a priming factor(s). The observation that the lavage fluid obtained from particulate-injected rabbits primed normal AM in vitro (FIGS. 1 and 2) indicates a priming factor(s) accumulates in the lungs of injected rabbits.

The priming mechanism discovered, which has a rapid and short term, represents a non-specific form of a cell-mediated defense system. The potential of more than a 100-fold increase in the oxidative responses of lung macrophages and the associated killing capacity will have a highly beneficial effect in controlling lung infections, as well as other infections, under circumstances in which classical cell-mediated immunity does not have time to develop.

It is anticipated that in situations where patients who are about to undergo a planned surgery, or where soldiers are about to undergo a planned invasion or encounter biological weaponry, or in any other situation contagion will be encountered, a person could be provided will either preparations of phagocytosable particles or preparations including a macrophage priming factor one to four days, and more preferably two to three days, prior to the event.

The administration of the particles could be by injection, inhalation of an aerosolized dose, or by other suitable means.

In view of the particle preparations which were effective in priming the macrophages for significantly enhanced activity in rabbits, a suitable dose range for administration to human beings would be between 0.5 and 2 mg per kg of body weight. These estimations are based on the rabbit data that would produce about 75% of the maximal response. It is expected that higher dosages may be possible. Providing enough particles for the maximal response would be a goal. It is critical that the particulates used for priming of macrophages be phagocytosable (e.g., between 0.3 and 5 µm in diameter). In view of the results above, almost any type of particle would be suitable for quickly priming macrophages to an enhanced killing potential. It is preferred that the particles be biodegradable. For example, suitable biodegradable particles would include: biodegradable microspheres that are compounds of L-lactic acid/glycolic acid homo- and co-polymers (see, Tabata et al., *J. Biomed. Mat. Res.* 22:837–858 (1988)); gelatin particles (cross-linked); degradable starch complexes; biodegradable hydrogel such as poly(2-hydroxy-ethyl-L-glutamine) (PHEG) (see, Merchant et al., *J. Biomed Mat. Res.* 17:301–325 (1983)); hydroxybutyrate-hydroxyvalerate copolymers (see, Yasin et al., *Biomaterials* 13:9–16 (1992)); concanavalin A; colloidal particles of organic origin; degradable polyesters including block copolymer poly(ethylene succinate)-b-poly(ethylene glycol) (PES/PEG) (see, Albertsson et al., *Acta Polymerica* 30:95–104 (1988)); chitin; and cellulose. If biodegradable particles are used, they should remain relatively intact in the body for the 1–4 days required optimum short-term priming of macrophages.

A major point of interest is that the interval required for maximal particle-induced priming coincides with the 3- to 4-day interval commonly observed as the period between bacterial contamination, colonization, and apparent infection following surgery. If priming of macrophages could be achieved during this interval, the risk of infection may be greatly reduced. Hence, patients which have been exposed to contagion (viruses or bacteria) could be provided with a suspension phagocytosable particles so that in the short term, the patient's macrophages could be primed for enhanced killing potential within a short time period (1–4 days).

There are two lines of rationale that support the proposition that a macrophage priming system might be helpful to cancer patients. First, it has been established that some tumors are destroyed by activated macrophages, especially sarcomas. Second, some tumors of lymphoid cell origin cause a marked immunodepression which can result in severe opportunistic infections. Hence, a system like that which has been disclosed which primes macrophages to a high level of anti-tumor activity as well as antimicrobial activity could have beneficial effects in such patients. In addition, the macrophage priming capability of the inventive system will be useful in patients suffering from the acquired immune difficiency syndrome (AIDS). AIDS and cancer patients have increased susceptibility to secondary infections and their macrophage system is usually preserved until very late stages in their disease. Therefore, this macrophage augmentation effect should be extremely useful in preventing and treating secondary and opportunistic infections. As the effects last one week and are expected to be non-toxic to tissue cells, the administration may be repeated at monthly intervals for both cancer and AIDS patients.

Particle preparations may be administered by intravenous or intraperitoneal injection. The preparations may be prepared in saline as well as conventional buffers to render the injectable particle suspensions isotonic.

Aerosol delivery of the particles might also be used (e.g. via a nebulizer or metered dose inhaler). A chief advantage of aerosolization of the particles would be the non-invasive delivery procedure. If the particles are formulated into a metered dose inhaler (MDI) for aerosol delivery to the lungs, it will need to be dispersed in a propellant and packaged in a canister under pressure. The propellant could be any or a combination of the commonly used freons or CFCs, such as $CCl_3F$ (Freon 11 or CFC-11), $CCl_2F_2$ (Freon 12 or CFC-12), and $CClF_2$-$CClF_2$ (Freon 114 or CFC-114). However, there has recently been much emphasis on using more ozone friendly propellants such as 1,1,1,2-tetrafluoroethane (HFC-134a) and propellant 227, hydrocarbons (propane, butane, isobutane, etc.), fluorocarbons (perfluoropentane), dimethyl ether, or the like, in MDI applications and any of these gases or combinations thereof could be used. As with almost all MDI applications, the propellant typically constitutes over 90% by weight of the composition mixture. Surfactants such as oleic acid, lecithin, sorbitan trioleate, and the like, might also be included for lubricating the metering valve and aiding in dispersing the particles within the mixture.

As discussed above, alternative preparations for short term priming of macrophages would include the macrophage priming factor released by cells in response to encountering the phagocytosable particles. As shown in FIGS. 1 and 2, a macrophage priming factor exists in BAL fluids from animals exposed to phagocytosable particles in vivo two or three days prior to harvesting AM. This macrophage priming factor could be obtained from fluids in animals pretreated with phagocytosable particles or by recombinant or other suitable techniques. Preparations containing the macrophage priming factor, similar to the particle preparations described above, could be prepared for delivery by aerosol, i.v. or i.p or i.t. injection, or by other suitable means. The macrophage priming factor would be dissolved or dispersed in a pharmaceutically acceptable carrier fluid or gas or binder or elixir which would facilitate providing the macrophage priming factor to the patient.

While the invention has been described in terms of its preferred embodiments, those skilled in the art will recognize that the invention can be practiced with modification within the spirit and scope of the appended claims.

Having thus described our invention, what we claim as new and desire to secure by Letters Patents is as follows:

1. A composition for enhancing non-specific cellular immunity, comprising:

a pharmaceutically acceptable carrier fluid which is injectable into a patient; and an effective amount sufficient to prime macrophages in said patient for an enhanced oxidative burst within four days after administration of non-toxic, phagocytosable, biodegradable particles having a size ranging from 0.3 μm to 5.0 μm in diameter dispersed in said carrier fluid, said biodegradable particles lacking biocides and pharmaceuticals and consisting solely of materials selected from the group consisting of L-lactic acid/glycolic acid homopolymers, L-lactic acid/glycolic acid copolymers, gelatin particles, degradable starch complexes, hydrogels, hydroxybutyrate-hydroxyvalerate co-polymers, polyesters, chitin, cellulose, and mixtures thereof.

2. The composition of claim 1 wherein said particles are colloidal particles of organic origin.

3. The composition of claim 1 wherein said particles are polyesters.

4. The composition of claim 1 wherein said particles are hydrogels.

5. The composition of claim 1 wherein said particles are chitin.

6. The composition of claim 1 wherein said particles are L-lactic acid and glycolic acid homo- and co-polymers.

7. The composition of claim 1 wherein said particles are gelatin particles.

8. The composition of claim 1 wherein said particles are degradable starch complexes.

9. The composition of claim 1 wherein said particles are hydroxybutyrate-hydroxyvalerate co-polymers.

10. The composition of claim 1 wherein said particles are cellulose.

11. A composition for enhancing non-specific cellular immunity, comprising:

a pharmaceutically acceptable carrier fluid which is injectable into a patient; and an effective amount sufficient to prime macrophages in said patient for an enhanced oxidative burst within four days after administration of phagocytosable particles having a size ranging from 0.3 μm to 5.0 μm in diameter dispersed in said carrier fluid, said particles lacking biocides and pharmaceuticals and consisting solely of materials selected from the group consisting of opsonized zymosan, polymethylmethacrylate, latex and polystyrene.

* * * * *